(12) United States Patent
Tsujii

(10) Patent No.: US 9,883,845 B2
(45) Date of Patent: Feb. 6, 2018

(54) RADIOGRAPHIC APPARATUS AND TOMOGRAPHIC APPARATUS

(71) Applicant: CANON KABUSHIKI KAISHA, Tokyo (JP)

(72) Inventor: Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 258 days.

(21) Appl. No.: 14/672,023

(22) Filed: Mar. 27, 2015

(65) Prior Publication Data

US 2015/0272536 A1 Oct. 1, 2015

(30) Foreign Application Priority Data

Mar. 31, 2014 (JP) .................. 2014-074569

(51) Int. Cl.
*A61B 6/04* (2006.01)
*A61B 6/00* (2006.01)
*A61B 6/03* (2006.01)

(52) U.S. Cl.
CPC .............. *A61B 6/502* (2013.01); *A61B 6/032* (2013.01); *A61B 6/4447* (2013.01); *A61B 6/0435* (2013.01)

(58) Field of Classification Search
CPC ..... A61B 6/032; A61B 6/0435; A61B 6/4447; A61B 6/502; A61B 6/482; A61B 6/0414; A61B 6/544; A61B 6/022; A61B 6/0457; A61B 6/4291; A61B 6/542; A61B 6/4241; A61B 6/4476; A61B 6/481; A61B 6/583; A61B 6/06; A61B 6/025; A61B 6/405; A61B 6/50; A61B 6/4258; A61B 6/466; A61B 6/4488; A61B 6/4021; A61B 6/541; A61B 6/107; A61B 6/4441; A61B 6/4452; A61B 90/17; A61B 10/0233; A61B 2090/364
USPC ..... 378/4, 17, 20, 37, 38, 68, 196, 208, 209
See application file for complete search history.

(56) References Cited

U.S. PATENT DOCUMENTS

| 2002/0122533 A1* | 9/2002 | Marie ................ A61B 6/502 378/196 |
| 2005/0171430 A1* | 8/2005 | Zhang ................ A61B 8/0825 600/437 |
| 2009/0080604 A1* | 3/2009 | Shores ................ A61B 6/032 378/37 |
| 2010/0080345 A1* | 4/2010 | Schilling ............ A61B 6/4275 378/37 |
| 2010/0177866 A1* | 7/2010 | Shibuya ............. A61B 6/032 378/20 |
| 2011/0021947 A1* | 1/2011 | Nakayama .......... A61B 6/0414 600/567 |

(Continued)

FOREIGN PATENT DOCUMENTS

WO 2006106927 A1 10/2006

*Primary Examiner* — Irakli Kiknadze
(74) *Attorney, Agent, or Firm* — Canon USA Inc., IP Division

(57) ABSTRACT

A radiographic apparatus includes a radiation source that emits radiation, a radiation detection unit that detects the radiation emitted from the radiation source, and having transmitted the object of a subject to be examined, a holding unit that holds the object to be examined between the radiation source and the radiation detection unit, and a control unit that performs control for determining an imaging condition, based on information related to the posture of the subject.

15 Claims, 7 Drawing Sheets

(56) References Cited

U.S. PATENT DOCUMENTS

2011/0182402 A1* 7/2011 Partain .................. A61B 6/032
378/9

* cited by examiner

RADIOGRAPHIC APPARATUS AND TOMOGRAPHIC APPARATUS

BACKGROUND OF THE INVENTION

Field of the Invention

The present invention relates to a radiographic apparatus and a tomographic apparatus.

Description of the Related Art

Image taking by radiation, especially, image taking by radiation in an breast examination is performed such that a subject as a patient takes various postures such as a standing position/sitting position/prone position according to the purpose of examination. For example, in a general health check, a burden on the patient is small and image taking time is short, and thus the posture of the standing position is selected. In a thorough examination accompanied with a biopsy, the prone position is selected in consideration of a need for more accurate details needed by a doctor or a technical expert.

International patent application publication WO 06/106927 A discloses a CT apparatus that supports a plurality of postures of the subject and is able to perform tomography of a breast.

However, in WO 06/106927 A, a relationship between the plurality of postures of the subject and an imaging condition corresponding thereto is not disclosed. Therefore, in WO 06/106927 A, it is difficult to perform image taking by radiation in a condition suitable for the posture of the subject.

Therefore, an objective of the present invention is to provide a radiographic apparatus that can perform image taking in an image condition suitable for the posture of the subject.

SUMMARY OF THE INVENTION

Therefore, the radiographic apparatus in the present invention includes a radiation source that emits radiation, a radiation detection unit that detects the radiation emitted from the radiation source, and having transmitted through an object of a subject to be examined, a holding unit for holding the object to be examined between the radiation source and the radiation detection unit, and a control unit that performs control for determining an imaging condition, based on information related to a posture of the subject.

Further features of the present invention will become apparent from the following description of exemplary embodiments (with reference to the attached drawings).

DESCRIPTION OF THE EMBODIMENTS

Hereinafter, embodiments of the present invention will be described in detail with reference to the drawings. Note that configuration elements described in the embodiments are merely exemplarily illustrated, and the technical scope of the present invention is not determined by the individual embodiments below, but is determined by claims.

First Embodiment

Figure 1:
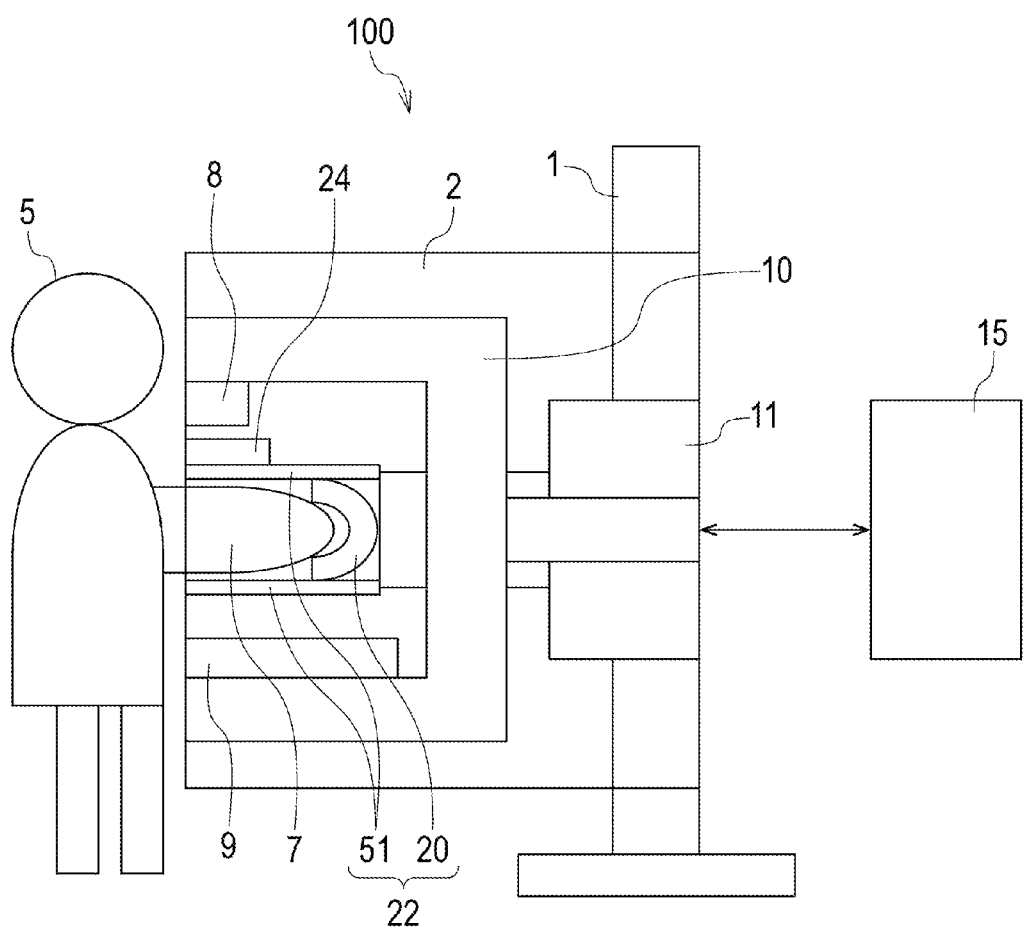
FIG. 1 is a diagram illustrating a configuration of a radiographic apparatus in a first embodiment.

FIG. 1 illustrates a configuration of a radiographic apparatus 100 in a first embodiment. The radiographic apparatus 100 illustrated in FIG. 1 is configured from an elevator 1, a main unit 2, and a control unit 15. The elevator 1 supports the main unit 2 so that the main unit 2 is lifted or lowered according to usage need. Then, the main unit 2 supports a radiation source 8, a radiation detection unit 9, and a holding unit 22. Further, the main unit 2 includes a filter 24. The filter 24 is arranged between the radiation source 8 and an object 7 to be examined. Further, the radiographic apparatus 100 includes the holding unit 22 for holding the object 7 between the radiation source 8 and the radiation detection unit 9. Then, the holding unit 22 includes at least one of a pressing holding unit 30 (illustrated in FIGS. 4A and 4B) that presses and holds the object 7 to be examined, and a suction holding unit 20 that suctions and holds the object to be examined. The pressing holding unit 30 and the suction holding unit 20 are detachably connected to the main unit 2. Further, the holding unit 22 includes an inner face holding unit 51 fixed to the main unit 2. Hereinafter, a space covered with the inner face holding unit 51, and in which the object 7 to be examined is arranged is described as an "image taking region". Further, the radiation source 8 and the radiation detection unit 9 are arranged in a fixing unit 10 to face each other across the object 7 to be examined. Then, the radiographic apparatus 100 includes a base rotating unit 11 that rotates the fixing unit 10 around the object 7 to be examined. The base rotating unit 11 is connected with the main unit 2. The control unit 15 performs control of the overall system of the radiographic apparatus 100. The control unit 15 then may determine an imaging condition including at least one of a holding state and a holding system of the object 7 to be examined by the holding unit 22, based on information related to the posture of the subject 5. The control unit 15 then controls at least one of the radiation source 8, the radiation detection unit 9, and the holding unit 22 according to the determined holding state and holding system. Here, the holding system refers to a method of holding the object 7 to be examined, and can include a holding method determined by a type of the holding unit 22 being used, and a case of not being held by the holding unit 22. Here, the holding state indicates a state of holding or a condition of holding the object 7 to be examined, and includes intensity of suction or force of pressing, for example.

Figure 2:
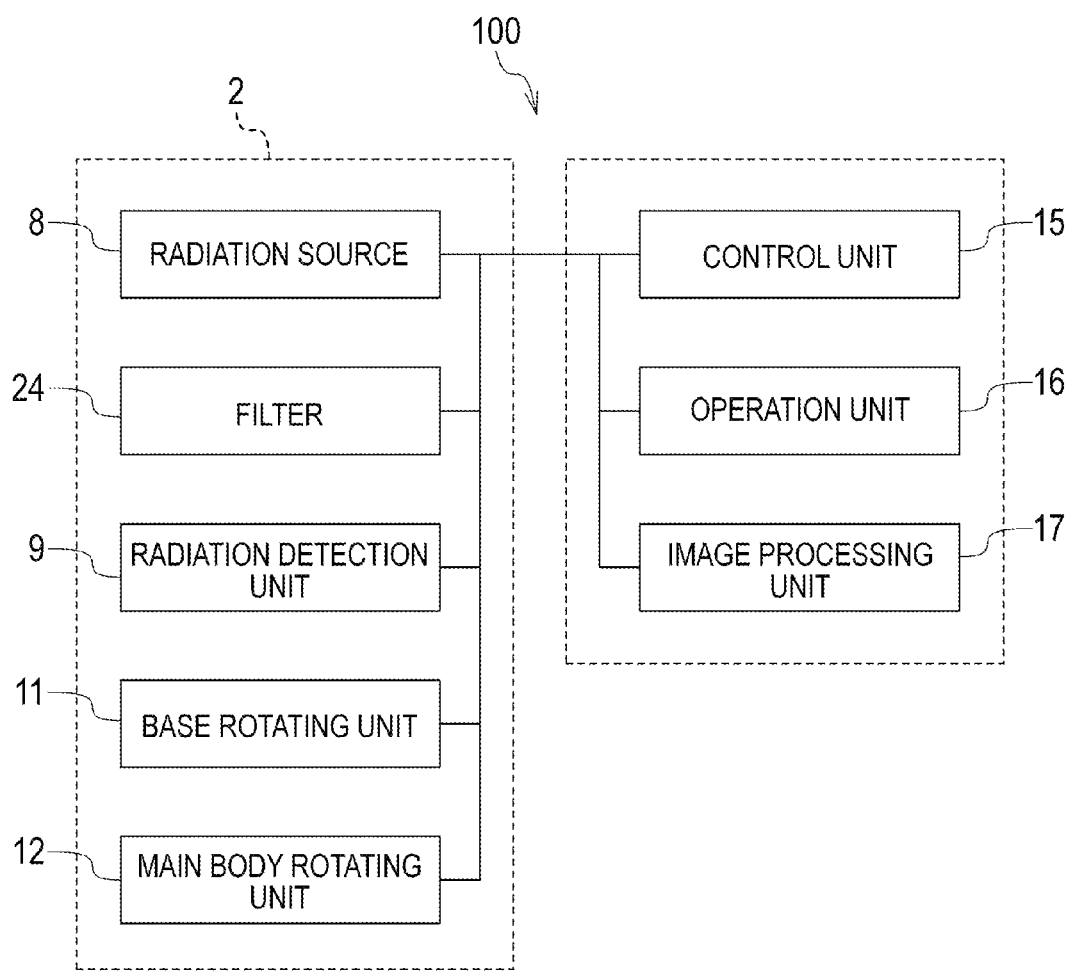
FIG. 2 is a diagram illustrating a functional configuration of the radiographic apparatus in the first embodiment.

Next, a functional configuration of the radiographic apparatus 100 will be described with reference to FIG. 2. FIG. 2 is a block diagram illustrating a functional configuration of the radiographic apparatus 100. The radiation source 8 emits radiation with predetermined intensity of radiation, and the object 7 to be examined can be irradiated with the radiation. The intensity of radiation is controlled by the control unit 15. The radiation source 8 is, for example, an X-ray tube which generates X ray radiation according to an input received from a high-voltage generation unit to the X-ray tube. Here, the x-ray tube input defines an output (intensity and duration) of the X ray radiation output from the X-ray tube. The input can include an X-ray tube voltage, an X-ray tube current, and the like. The intensity of radiation is determined with the X-ray tube input from the high-voltage generation unit by the control unit 15. The intensity of radiation is the magnitude of an amount of irradiated radiation emitted from the radiation source 8. Note that the radiation source 8 can include the high-voltage generation unit together with the X-ray tube.

The radiation detection unit 9 detects the radiation that has transmitted through the object 7 to be examined to generate image data. The image data is acquired by the control unit 15, and is transmitted to an image processing unit when a tomographic image is generated. For example, the radiation detection unit 9 includes a flat panel detector (FPD) and a data generation unit. The FPD includes a plurality of pixels made of known semiconductor elements. The data generation unit generates image data according to electric charges acquired from the respective pixels. Then, the image data is transmitted to an image processing unit 17. The pixel size of each pixel can be changed by the control unit 15 according to an imaging condition.

The filter 24 has a function to adjust distribution of the amount of transmitted radiation by which the radiation emitted from the radiation source 8 is transmitted. As examples of the function to adjust the amount of transmitted radiation, the filter 24 has a function to limit an irradiation field of the radiation, and a function to cause the amount of transmitted radiation detected by the radiation detection unit 9 to become constant. To be specific, as the filter 24, a wedge filter, an added filter, and a collimator are favorably used. Since the shape of the object 7 to be examined is changed according to the posture of the subject 5, the filter 24 is appropriately selected at the time of taking an image. Then, the shape of a subject to be imaged depends on the holding state and the holding system of the holding unit 22. Therefore, the filter 24 is determined according to the holding system. The control unit 15 performs control for selecting and changing the filter 24. For example, one filter 24 can be selected by the control unit 15 from among a plurality of filters configured in the radiographic apparatus 100 in advance. Meanwhile, as another method of selecting the filter 24, the control unit 15 can determine a combination of a plurality of materials that absorbs the radiation, and change the shape of the filter 24.

The base rotating unit 11 includes a mechanism for rotating the fixing unit 10. The radiographic apparatus 100 can take an image while rotating the fixing unit 10 by the base rotating unit 11, and thus can take images of the object 7 to be examined from a plurality of different angles. The base rotating unit 11 receives a control command from the control unit 15, and rotates the fixing unit 10 by a predetermined angle. As the rotating mechanism, for example, a driving mechanism such as a motor, and mechanical parts such as a gear and a rack. Further, an encoder and the like may be included in order to detect an amount of relative rotation between the base rotating unit 11 and the fixing unit 10. Meanwhile, a sensor may be included in order to detect predetermined rotated positions of the base rotating unit 11 and the fixing unit 10. As the sensor, various sensors that detect an electric field or a magnetic field can be used.

A main body rotating unit 12 includes a mechanism for rotating the main unit 2. The main body rotating unit 12 can incline the main unit 2 with respect to an elevating direction of the elevator 1 by rotating the main unit 2 by a desired angle with respect to the elevating direction. The desired angle can be determined according to the posture of the subject 5. The main body rotating unit 12 can rotate the main unit 2 to the desired angle according to the posture of the subject 5. The main body rotating unit 12 is configured from a driving mechanism such as a motor, and mechanical parts such as a gear and a rack. Further, an encoder and the like may be included in order to detect an amount of relative rotation between the main body rotating unit 12 and the elevator 1. Further, a sensor for detecting desired rotated positions may be included instead of one that directly detects the amount of relative rotation between the main body rotating unit 12 and the elevator 1. As the sensor, various sensors that detect an electric field or a magnetic field can be used. The control unit 15 can detect the angle of the main unit 2 by acquiring the amount of rotation of the main body rotating unit 12 by the detecting means, and can acquire information related to the posture of the subject 5.

The control unit 15 can control an operation of the entire radiographic apparatus 100. As an example, the control unit 15 is configured from hardware, such as a computer including a microprocessor or central processing unit (CPU) and related circuitry necessary to operate the radiographic apparatus 100. The control unit 15 selects an imaging condition, based on the information related to the posture of the subject 5, and generates control command to respective units of the radiographic apparatus 100. Then, the respective units can perform operations based on the control commands. Here, the subject 5 is a patient having a portion to be taken as the object 7 to be examined, an image of which is taken by the radiographic apparatus 100. The imaging condition is a condition for performing radiation image taking. The imaging condition includes at least the holding state and the holding system of the holding unit. Further, the imaging condition can include the intensity of the radiation, the radiation detection unit, and the filter. The information related to the posture of the subject is information including a posture of when an image of the subject 5 is taken. Examples of the posture include, but are not limited to, the standing position, the prone position, a side-lying position, and the sitting position. Further, the control unit 15 can at least acquire information about whether the subject 5 is in the standing position or the prone position. Then, the control unit 15 can acquire the information of the posture of the subject 5, based on information input by the user through the operation unit 16. As described above, the control unit 15 can acquire the information of the posture of the subject 5, based on a rotation angle of the main body rotating unit 12. The control unit 15 can select the imaging condition, based on the information related to the posture, by corresponding to the rotation angle of the main body rotating unit 12 and the posture with which an image of the subject 5 is taken, to each other.

The operation unit 16 is connected to the control unit 15. The operation unit 16 is a user interface (UI) such as a mouse, a keyboard, and a touch panel, and outputs a signal according to an operation to the control unit. The user inputs the information related to the posture of the subject 5 through the operation unit 16, and outputs the information to the control unit 15.

An image processing unit 17 can perform preprocessing necessary for performing reconstruction such as offset correction, gain correction, defect correction, or logarithmic transformation, with respect to the image data acquired in the radiation detection unit 9. The image processing unit 17 then performs image reconstruction, and generates a tomographic image. An algorithm used for the image reconstruction is not especially limited, and analytical reconstruction such as a filtered back projection method, algebraic reconstruction using an inverse matrix or a sequential method, or the like can be used.

The holding unit 22 will be described. The holding unit 22 has a function to hold the object 7 to be examined in a predetermined shape. The holding unit 22 can decrease in an influence of a movement of the subject 5 or involuntary movement at the time of the radiation image taking by the function. Note that, in the present embodiment, the object 7 to be examined is, but not limited to, a breast. To decrease attenuation of the radiation due to transmission of the radiation by the holding unit 22, the holding unit 22 is configured from a material having a high radiation transmission rate. The holding unit 22 includes at least one of the pressing holding unit 30 that presses and holds the breast, the suction holding unit 20 that suctions and holds the object 7 to be examined, and the inner face holding unit 51 that can hold the breast with a holding system different from the suction and pressing. Further, the pressing holding unit 30 and the suction holding unit 20 are detachably connected to the main unit 2. The inner face holding unit 51 is arranged and fixed as a part of an inner face of the main unit 2. Note that the inner face holding unit 51 functions as a cover that forms a bore diameter of the main unit 2. The control unit 15 can control an attached/detached state of the holding unit 22 by controlling the main unit 2. To connect and hold the pressing holding unit 30 and the suction holding unit 20, and the main unit 2, for example, an electromagnet is provided in both of the main unit 2 and the pressing holding unit 30, and the suction holding unit 20, whereby the pressing holding unit 30 and the suction holding unit 20, and the main unit 2 can be fixed by magnetic force. Further, the holding unit 22 and the main unit 2 are mechanically connected, and the control unit 15 can control a connected state. Further, as the holding system different from the suction and pressing, the system does not hold the object 7 to be examined by the holding unit 22 according to the posture of the subject 5 or the size of the breast. With the configuration, the radiation image taking can be performed by an appropriate holding unit according to the posture of the subject.

Figure 3A:
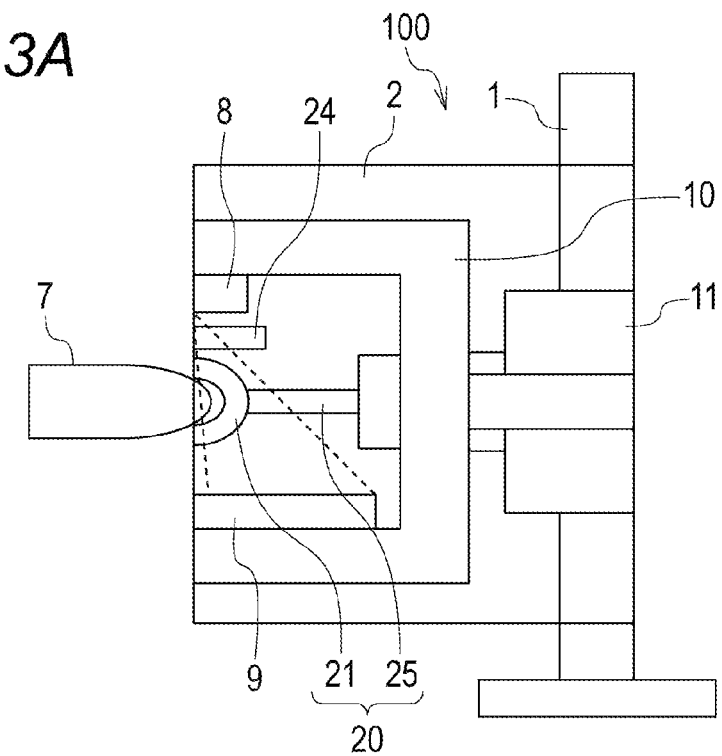
FIGS. 3A and 3B are diagrams illustrating examples of a suction holding unit of the radiographic apparatus in the first embodiment.
Figure 3B:
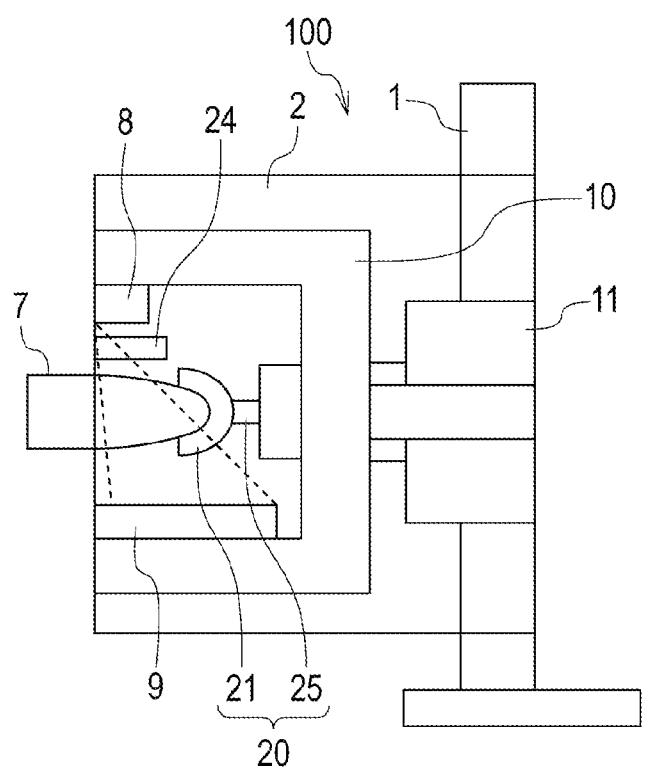

FIGS. 3A and 3B illustrate diagrams illustrating the suction holding unit 20 as an example of the holding unit 22. Note that FIGS. 3A and 3B are diagrams from which the subject 5 and the inner face holding unit 51 are omitted. The suction holding unit 20 is detachably connected to the main unit 2. The suction holding unit 20 includes a suction cup 21 and a draw-in ball screw 25. The draw-in ball screw 25 is a driving mechanism, and can move the suction cup 21 to an inside and an outside of the image taking region. Note that the draw-in ball screw 25 is not limited thereto as long as one can move the suction cup 21 to the inside and the outside of the image taking region. When moving the suction cup 21 to the inside and the outside of the image taking region, the movement may be performed by manipulation of a user (not illustrated). However, a control unit 109 may electrically control and move the suction cup 21. FIG. 3A illustrates a state in which the suction cup 21 is mounted to the bread that is the object 7 to be examined. With the draw-in ball screw 25, the suction cup 21 is moved to a position where the subject 5 can mount the suction cup 21 to the breast. The breast of the subject 5 is inserted into the suction cup 21, and the air in the suction cup 21 is decompressed by a decompression unit (not illustrated), so that the breast is fixed inside the suction cup 21. Control of the decompression unit is performed by the control unit 109. FIG. 3B illustrates a state in which the radiographic apparatus 100 holds the breast by the suction cup 21, and can take an image of the breast. The breast is held in the suction cup 21, and the suction cup 21 is then drawn into an image taking region of the main unit 2 by the draw-in ball screw 25. Note that the method of fixing the breast is not limited to the above procedure. After the suction cup 21 is drawn into and fixed to the image taking region, the breast may be inserted and decompressed. The section shape of the suction cup 21 is a circle or an ellipse. Since the suction cup 21 has the shape, the thickness of the breast becomes approximately uniform when image taking directions are different in tomography, change of the amount of transmitted radiation can be decreased, and generation of a tomographic image becomes easy. Further, the user can select the suction cup 21 having an appropriate shape according to the shape of the breast. Therefore, the holding unit 22 can hold the breast regardless of the shape of the breast.

Figure 4A:
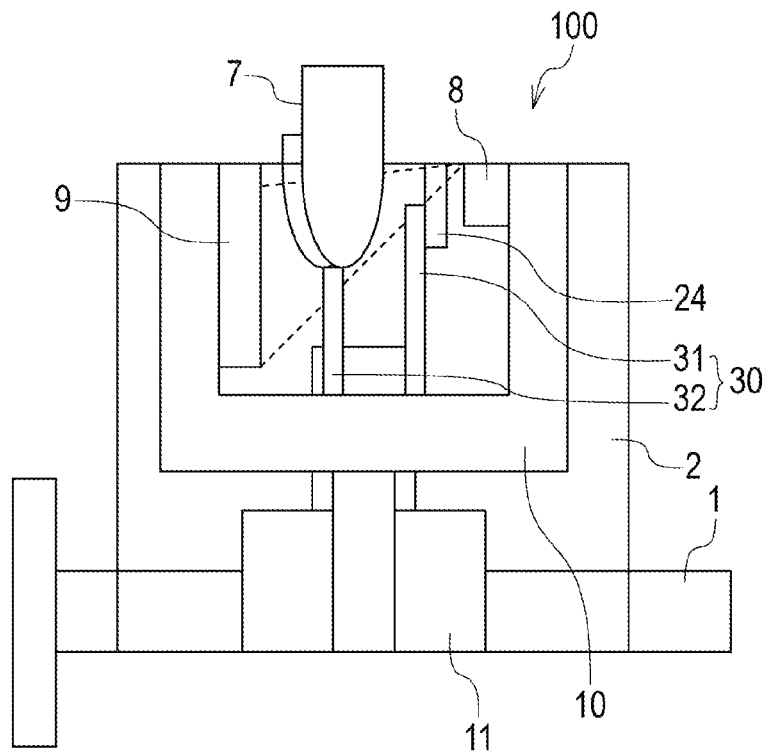
FIGS. 4A and 4B are diagrams illustrating examples of a pressing holding unit of the radiographic apparatus in the first embodiment.
Figure 4B:
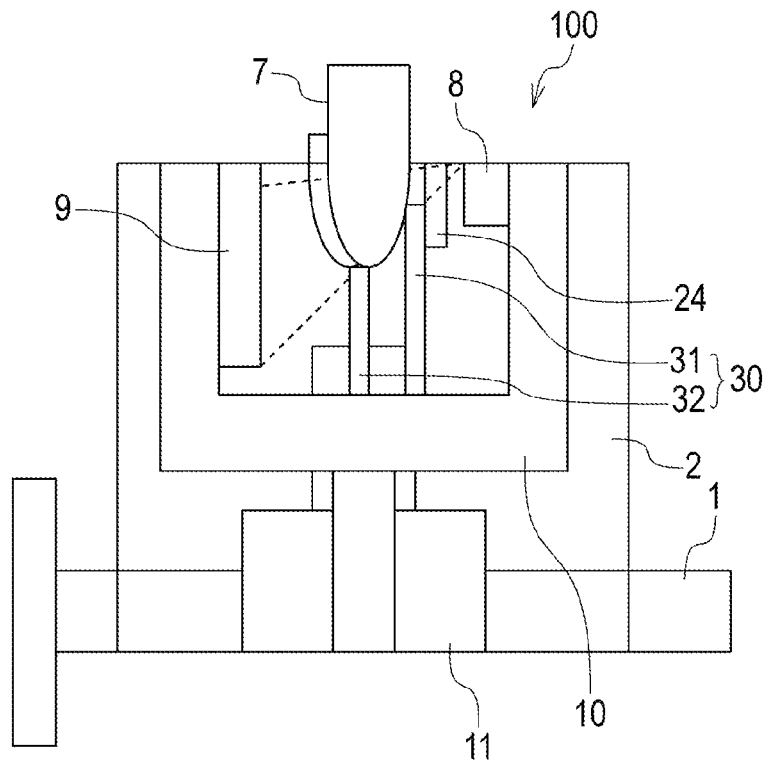

FIGS. 4A and 4B are diagrams illustrating the pressing holding unit 30 as an example of the holding unit 22. In FIGS. 4A and 4B, the inner face holding unit 51 is not illustrated. The radiographic apparatus 100 includes the pressing holding unit 30, and can hold the breast by interposing the breast by pressing panels 32. The pressing holding unit 30 includes a pressing base 31 and the pressing panels 32. The pressing holding unit 30 can hold the breast by pressing the pressing panels 32 against the pressing base 31. Note that, as the pressing holding unit 30, a method of combining and arranging a plurality of the pressing panels 32 on an arc, or a method of combining a plurality of the pressing panels 32 having curved surfaces such that the curved surfaces are layered may be used. Further, the inner face holding unit 51 in FIGS. 3A and 3B will be described. The inner face holding unit 51 is fixed to the main unit 2, and the decompression unit (not illustrated) is connected to the inner face holding unit 51. The inner face holding unit 51 can hold the breast by decompressing the air in the image taking region by the connected decompression unit. Holding by the inner face holding unit 51 does not use the suction holding unit 20 and the pressing holding unit 30. Therefore, an influence of attenuation and scattering of the radiation can be decreased. The radiographic apparatus 100 can freely combine the above-described various holding units 22.

Figure 5A:
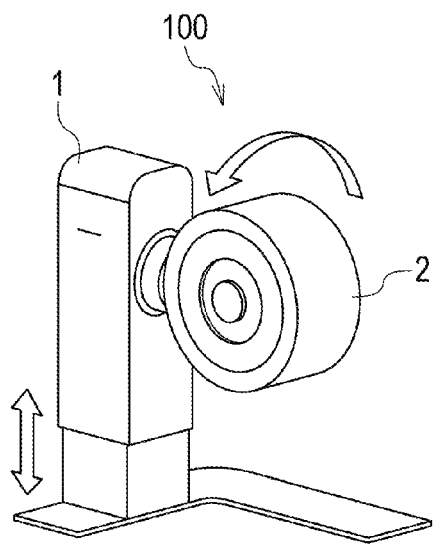
FIGS. 5A to 5C are diagrams illustrating states in which the radiographic apparatus in the first embodiment supports various postures.
Figure 5B:
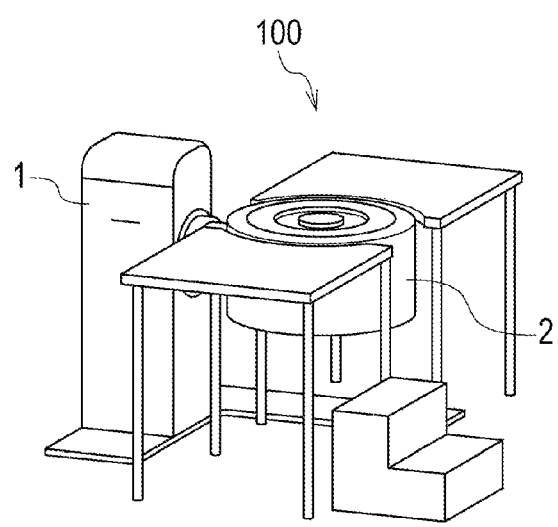
Figure 5C:
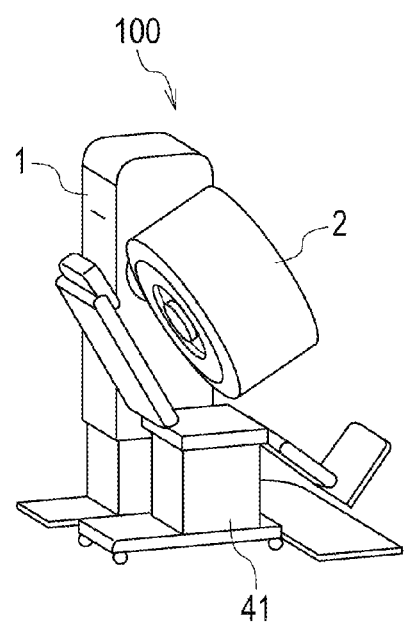

FIGS. 5A to 5C illustrate the radiographic apparatus 100 in states corresponding to various postures. Note that, in FIGS. 5A to 5C, the subject 5 is not illustrated. The radiographic apparatus 100 can change the angle according to the posture of the subject at the time of image taking. In the radiographic apparatus 100, the state of FIG. 5A is a reference position (0 degrees) of the rotation angle. In the case of the image taking in the standing position, the radiographic apparatus 100 is used in the state illustrated in FIG. 5A. In the case of the image taking in the prone position, the radiographic apparatus 100 is used in the state of FIG. 5B. In this case, the main unit 2 is rotated by 90 degrees in the right direction. Further, the main unit 2 has a connection portion (not illustrated), and can connect a bed unit 3. In this case, the subject 5 gets on the top of the bed unit 3, and can take a posture of the prone position. The main unit 2 and the bed unit 3 are connected not to have a step at the time of radiation image taking. Then, the subject 5 inserts the breast into the image taking region of the main unit 2, whereby the radiation image taking can be performed. Note that the radiographic apparatus 100 can take an image in the sitting position by further rotating the main unit 2, as illustrated in FIG. 5C. It is favorable to include a chair 41 in the image taking in the sitting position. Note that, in the state of FIG. 5B, the main unit 2 and the bed unit 3 may have a structure of being connected and elevated. As described above, the radiographic apparatus 100 can take an image corresponding to the various postures. Note that the angle of the main unit 2 illustrated here is a representative angle, and the angle can be appropriately finely adjusted according to the physical size or the physical shape of the subject. Further, a reference angle can be appropriately changed according to an installation environment and a use status.

Hereinafter, favorably imaging conditions set according to the postures illustrated in FIGS. 5A to 5C will be described. First of all, the favorable imaging condition in the standing position will be described. The radiographic apparatus 100 performs image taking in the standing position mainly in image taking for health check. The radiographic apparatus 100 can make patient throughput higher than other postures by enabling the image taking in the standing position. Since the breast is deformed by an own weight at the image taking in the standing position image taking, it is desirable to hold the breast in a predetermined shape by the holding unit 22. The control unit 15 selects the suction holding unit 20 as the holding unit 22. In this case, the control unit 15 selects the intensity of radiation and the filter 24 according to the shape of the held breast. The control unit 15 selects the filter 24 corresponding to the shape of the suction holding unit 20 as the filter 24 to be used in the radiation image taking. Further, the control unit 15 selects the intensity of radiation corresponding to the suction holding unit 20 and the filter 24. Further, the control unit 15 can select the inner face holding unit 51 without using the suction holding unit 20. In this case, it is favorable to decompress the inside of the inner face holding unit 51 to hold the shape of the breast. As described above, the control unit 15 can select the imaging condition suitable for the image taking in the standing position image taking.

Next, the favorably imaging condition in the prone position will be described. The image taking in the prone position is used in a thorough examination, in addition to the use of health check. An example of the thorough examination is a biopsy in which tissue of a lesioned part in the breast is collected while the radiation image taking is performed. Further, the image taking in the prone position is effective to the subject 5 having difficulty in taking a posture of the standing position or the sitting position. The image taking in the prone position can be performed in a holding system of natural drop. The image taking in the prone position can be performed without holding the breast by the holding unit 22 because the breast as the object 7 to be examined naturally drops due to gravity, and the shape becomes constant. Further, the image taking in the prone position can be performed with respect to the breast up to the vicinity of a breast wall portion because the breast naturally drops. Further, in the image taking in the prone position, the posture of the subject 5 can be more easily stabilized than the image taking in the standing position. Further, the breast can be held by the inner face holding unit 51. In the image taking in the prone position, the shape is defined by natural drop. Therefore, decompression by the inner face holding unit 51 is not necessary. As another method of taking an image, the breast can be held by the suction holding unit 20 and an image can be taken, even at the time of taking an image in the prone position. The section shape of the breast is defined even with the subject 5 having a breast different in suction and holding. When the breast naturally drops without being held by the holding unit 22, the cross section of the breast becomes large, and the length of the breast becomes short. Therefore, the control unit 15 sets the intensity of radiation large in accordance with the cross section of the breast. Further, the cross section of the breast in the pressing direction becomes small when being held by the pressing holding unit 30. However, the cross section of the breast in the direction of the face to be pressed becomes large, and the length of the breast becomes long. As described above, the section shape of the object 7 to be examined is changed with the change of the posture of the subject 5. Therefore, the control unit 15 selects the filter 24 according to the holding state and the holding system of the breast. Further, the control unit 15 selects the intensity of radiation suitable for the holding unit 22 and the filter 24. In this case, the control unit 15 selects the filter 24 through which the amount of transmitted radiation to the radiation detection unit 9 becomes uniform. With the configuration, the control unit 15 can select the imaging condition suitable for the image taking in the prone position.

Another imaging condition will be described. The pixel size of the image data acquired in the radiation detection unit 9 when tomography is performed will be described. In the thorough examination, a high-definition image is required in order to accurately determine benign/malignant and a region of tissue to be collected. In the case of the thorough examination, the control unit 15 determines the intensity of radiation of the radiation source 8, based on the size of the cross section of the taken image, and accuracy of the required image (pixel resolution). Then, the control unit 15 changes setting of pixel addition and the like in the radiation detection unit 9, and determines the pixel size.

As described above, the imaging condition suitable for the posture of the subject 5 has been described using the standing position and the prone position as examples. However, the embodiment is not limited to the example. As other postures, the sitting position, or a dorsal position may be employed. In this case, the imaging condition can be set according to the posture of the subject 5, the object 7 to be examined, and the holding system determined based on the posture and the object 7 to be examined. Further, magnitude relationship of the imaging conditions is an example, and may be changed according to the material quality of the holding unit 22, the section shape of the object 7 to be examined, the material quality or the shape of the filter 24, or a spectrum of the radiation source 8 to be used.

Figure 6:
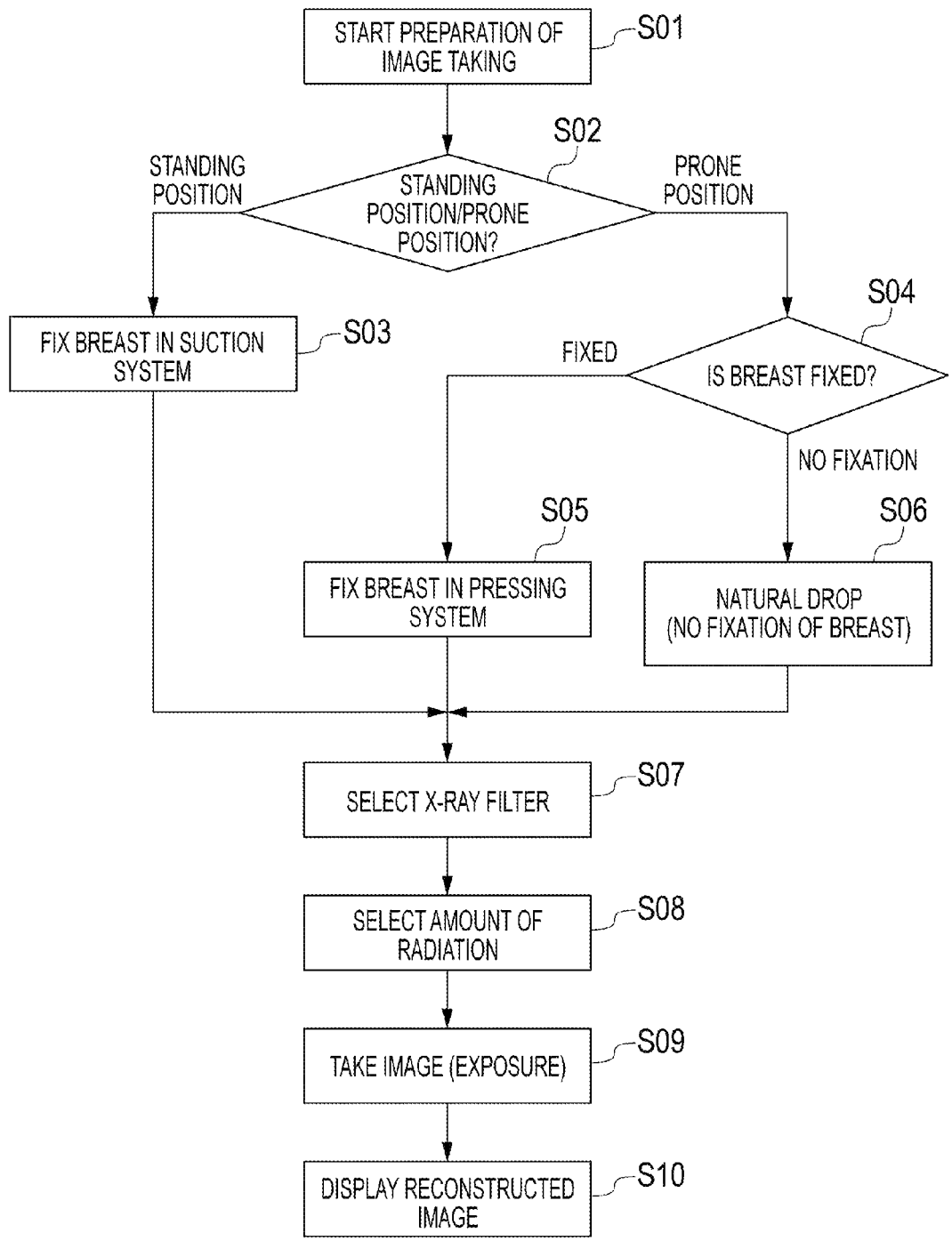
FIG. 6 is a flowchart at the time of setting a condition of the radiographic apparatus in the first embodiment.

FIG. 6 is a diagram illustrating a flow of processing of the radiographic apparatus 100 of the present embodiment at the time of image taking. First of all, at step S01, preparation of the image taking is performed. Here, the user causes the subject 5 to take a posture with which the image taking can be performed. Next, at step S02, the control unit 15 acquires the information related to the posture of the subject 5, and determines whether the image taking in the standing position or in the prone position. When the image taking in the standing position is selected, the control unit 15 connects and fixes the suction holding unit 20 to the main unit 2 (S03). At step S03, the user connects the suction cup 21 corresponding to the size of the breast of the subject 5 to the suction holding unit 20. The user can select the inner face holding unit 51 without using the suction cup 21. Next, in the case of the image taking in the prone position, the control unit 15 determines whether holding the breast (S04). When having selected to hold the breast, the control unit 15 performs control of connecting the pressing holding unit 30 to the main unit 2 (S05). In this case, the user uses the pressing base 31 and the pressing panels 32 corresponding to the breast size of the subject 5. When not fixing the breast, the user removes the attached holding unit (S06). The filter 24 is selected corresponding to existence/non-existence of the suction holding unit 20, the system, and the size. The control unit 15 determines the intensity of radiation, corresponding to the selected filter 24 (S08). When performing tomography, the intensity of radiation also depends on resolution of a reconstructed image. Therefore, the control unit 15 sets the intensity of radiation high when a highly precise image is required. Then, the control unit 15 controls the radiation source to irradiate the breast with the radiation to perform the radiation image taking (S09). When performing the tomography, the control unit 15 controls the apparatus to take images of the breast from a plurality of different angles. Following that, the control unit 15 controls a display unit (not illustrated) to display an image subjected to the image processing in the image processing unit 17 (S10). Note that the flow of the processing is an example, and is not limited thereto. For example, as the holding unit 22, the suction holding unit 20 can be used in any case, or only the inner face holding unit 51 can be used instead of the suction holding unit 20 in any posture. Further, the procedures can be appropriately switched.

As described above, the radiographic apparatus that determines the imaging condition suitable for the posture of the subject 5 can be provided.

Second Embodiment

A configuration of a radiographic apparatus 100 in a second embodiment will be described with reference to FIGS. 7A to 7C. A favorable embodiment in a radiographic apparatus accompanied with a biomaterial examination (biopsy) that is one of thorough examination will be described. A difference from the first embodiment is that an opening 4, which is a part of the main unit 2 being able to be open, is included in a position where an object 7 to be examined can be observed. Hereinafter, details of the second embodiment will be described.

Figure 7A:
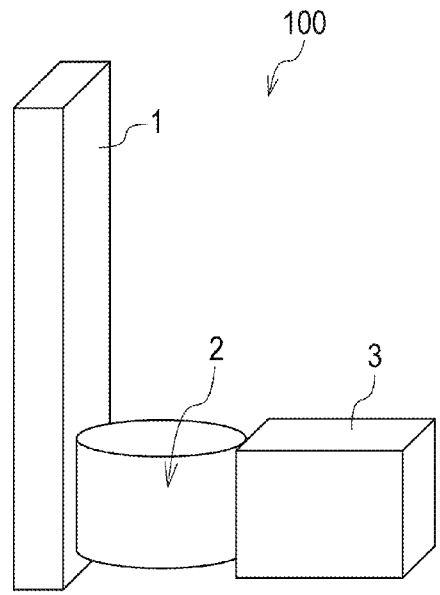
FIGS. 7A to 7C are diagrams illustrating configurations of a radiographic apparatus in a second embodiment.
Figure 7B:
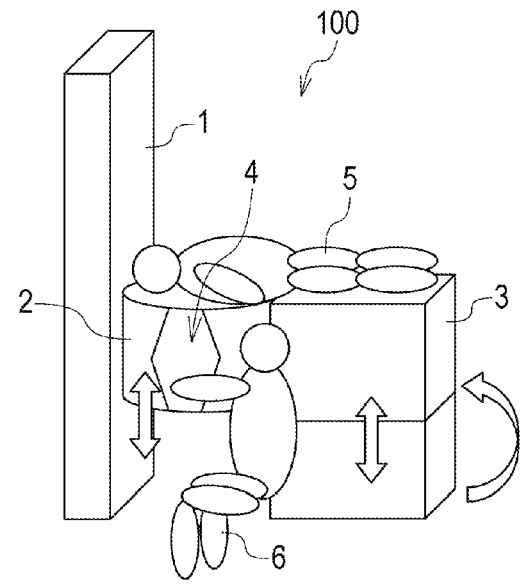
Figure 7C:
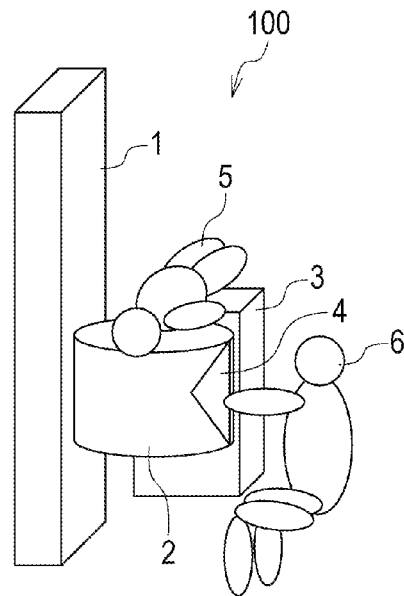

The main unit 2 in the radiographic apparatus 100 illustrated in FIGS. 7A to 7C includes a first face having an opening for a holding unit 22, a second face facing the first face, and an outer face that connects the first face and the second face. Further, the outer face includes the opening 4, which is a part of the outer face being able to be open at a position where the object 7 to be examined can be observed. The opening 4 is open to a biopsy portion of the breast that is the object 7 to be examined when manipulation of the biopsy is performed, so that the manipulation of a user 6 to the breast that is the object 7 to be examined becomes possible. Then, the opening 4 is closed at the time of radiation image taking. Note that the use of the opening 4 is not limited to the case where the manipulation is performed to a breast. For example, the opening 4 can be used when the user 6 observes a state of the breast at the time of image taking in a prone position. The position of the opening 4 in the outer face is favorably a portion different from a connection portion of the main unit 2 and a bed unit 3. Further, the opening 4 has a different favorable position depending on whether which of right and left breasts is manipulated. FIG. 7B illustrates a case in which an image of the left side breast of a subject 5 is taken and the left side breast is manipulated. In this case, the opening 4 is included in the right side toward an elevator 1. Meanwhile, in FIG. 7C, when the bed unit 3 is arranged with respect to the elevator 1 and the main unit 2, the opening 4 is included in a position facing the elevator 1.

A favorable condition in the radiographic apparatus 100 that supports a biopsy will be described. In the radiographic apparatus 100, radiation image taking and tomography are performed in order to identify a place to be punctured on an image. To cause a puncture needle 40 to enter the breast in the process of a biopsy, a pressing holding unit 30 illustrated in FIGS. 4A and 4B is suitable, rather than a suction holding unit 20 that covers the periphery of the breast. When the breast is held by the pressing holding unit 30, the breast can be held in a state where at least a part of the periphery of the breast is exposed. Therefore, the user 6 can cause the puncture needle 40 to easily enter the breast. Further, pressing panels 32 and a pressing base 31 press the breast such that pressed curve surfaces become a circle. Therefore, the amount of transmitted radiation cannot be substantially changed in each projection direction in tomography. Further, the pressing and holding is not limited to a plurality of curved surfaces, and a combination of a curved surface and a flat surface may be employed. Then, a control unit 15 can set an imaging condition, based on the shape of the breast held by the holding unit.

With the configuration, the imaging condition based on the posture of the subject 5 can be set, and the radiographic apparatus that supports a biopsy can be provided.

Certain aspects disclosed in the embodiment(s) of the present invention can also be realized by one or more circuits (e.g., application specific integrated circuit (ASIC)) or a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s). For example, a method or steps thereof may be performed by one or more circuits (e.g., application specific integrated circuit (ASIC)) or by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-074569, filed Mar. 31, 2014, which is hereby incorporated by reference herein in its entirety.

What is claimed is:

1. A radiographic apparatus for imaging a plurality of positions of a subject comprising:
   a radiation source configured to emit radiation;
   a radiation detection unit configured to detect the radiation emitted from the radiation source and transmitted through an object to be examined of the subject;

a holding unit configured to hold the object to be examined between the radiation source and the radiation detection unit; and a control unit configured to perform control for determining a holding state of the object to be examined by the holding unit based on a position of the subject and an imaging condition based on the holding state of the object, wherein the control unit sets an intensity of the radiation larger in accordance with the cross section of the object which naturally drops without being held by the holding unit in a case of imaging with a prone position than that in a case of imaging with a standing position.

2. The radiographic apparatus according to claim 1, wherein the imaging condition includes at least one of the intensity of the radiation emitted from the radiation source, a pixel size of the radiation detection unit, and a filter disposed between the radiation source and the object which adjusts an amount of radiation transmitted therethrough.

3. The radiographic apparatus according to claim 1, further comprising:

a main unit that supports the radiation source, the radiation detection unit, and the holding unit, wherein the holding unit includes at least one of a pressing holding unit that presses and holds the object to be examined, a suction holding unit that suctions and holds the object to be examined, and an inner face holding unit configured to hold the object to be examined with a holding system different from the suction holding unit and pressing holding unit, wherein the pressing holding unit and the suction holding unit are detachably connected to the main unit.

4. The radiographic apparatus according to claim 3, wherein the control unit selects at least one of holding the object to be examined by the pressing holding unit, holding the object to be examined by the suction holding unit, and not performing the holding of the object to be examined using the pressing holding unit and the suction holding unit, based on the information related to a posture of the subject.

5. The radiographic apparatus according to claim 3, further comprising:

an elevator that supports the main unit so that the main unit is elevated; and a main unit rotating unit configured to rotate the main unit with a desired angle with respect to an elevating direction of the elevator to incline the main unit with respect to the elevating direction, wherein the control unit determines the information related to a posture of the subject, based on an amount of rotation of the main unit rotated by the main body rotating unit.

6. The radiographic apparatus according to claim 3, wherein the main unit includes a first face having an opening for the holding unit, a second face facing the first face, and an outer face that connects the first face and the second face, and the outer face includes an opening, which is a part of the outer face being able to be open in a position where the object to be examined is able to be observed.

7. The radiographic apparatus according to claim 1, further comprising:

an operation unit through which a user inputs the information related to a posture of the subject, wherein the control unit acquires the information related to a posture of the subject from the operation unit.

8. The radiographic apparatus according to claim 1, wherein the control unit selects intensity of the radiation emitted from the radiation source, as the imaging condition, based on the information related to a posture of the subject.

9. The radiographic apparatus according to claim 1, further comprising:

a plurality of filters configured to adjust distribution of an amount of transmitted radiation by which the radiation emitted from the radiation source transmits, wherein the control unit selects one of the plurality of filters, as the imaging condition, based on the information related to a posture of the subject.

10. The radiographic apparatus according to claim 1, wherein the control unit determines a pixel size of the radiation detection unit, as the imaging condition, based on the information related to a posture of the subject.

11. The radiographic apparatus according to claim 1, wherein the information related to a posture of the subject includes information indicating that the position of the subject is at least one of the standing position, a sitting position, and a prone position.

12. The radiographic apparatus according to claim 1, wherein the object to be examined is a breast.

13. A tomographic apparatus comprising:

the radiographic apparatus according to claim 1; and an image processing unit configured to generate a tomographic image, based on images of the object to be examined taken with the radiation source and the radiation detection unit in the radiographic apparatus from a plurality of different angles.

14. A biopsy apparatus comprising:

the tomographic apparatus according to claim 13, wherein a part of the object to be examined is collected, based on the images of the object to be examined taken by the radiographic apparatus.

15. A radiation imaging method using a radiographic apparatus including a radiation source that emits radiation, a radiation detection unit that detects the radiation emitted from the radiation source transmitted through an object to be examined of a subject, and a control unit which controls the radiation source and the radiation detection unit, the method comprising:

holding the object to be examined, with a holding unit, between the radiation source and the radiation detection unit;

acquiring, by the control unit, information related to a position of the subject selected from a plurality of positions which include a standing position and a prone position;

determining, by the control unit, a holding state of the object to be examined being held by the holding unit based on a position of the subject and an imaging condition based on the holding state of the object; and performing a radiation imaging according to the holding state and the imaging condition, wherein the control unit sets an intensity of the radiation larger in accordance with the cross section of the object which naturally drops without being held by the holding unit in a case of imaging with a prone position than that in a case of imaging with a standing position.

* * * * *